United States Patent [19]

Gaffar et al.

[11] 4,152,420
[45] * May 1, 1979

[54] ANTICALCULUS ORAL COMPOSITION

[75] Inventors: Abdul Gaffar, Somerset; Stuart D. Friedman, Bound Brook, both of N.J.

[73] Assignee: Colgate-Palmolive Company, New York, N.Y.

[*] Notice: The portion of the term of this patent subsequent to Aug. 29, 1995, has been disclaimed.

[21] Appl. No.: 928,922

[22] Filed: Jul. 28, 1978

Related U.S. Application Data

[63] Continuation-in-part of Ser. No. 755,895, Dec. 30, 1976, Pat. No. 4,110,429.

[51] Int. Cl.² ............................................. A61K 7/16
[52] U.S. Cl. .................................... 424/56; 424/49; 424/52
[58] Field of Search .............................. 424/49–58; 260/465.4

[56] References Cited

U.S. PATENT DOCUMENTS

| 3,498,943 | 3/1970 | Dannals | 260/29.6 |
|---|---|---|---|
| 3,646,099 | 2/1972 | Dannals | 260/465.4 |
| 3,668,230 | 6/1972 | Dannals | 260/465.4 |
| 3,859,260 | 1/1975 | Dannals | 260/79.3 R |
| 4,110,429 | 8/1978 | Gaffar et al. | 424/54 |

FOREIGN PATENT DOCUMENTS

| 853266 | 10/1970 | Canada. |
| 1800373 | 5/1969 | Fed. Rep. of Germany. |
| 1957384 | 6/1970 | Fed. Rep. of Germany. |
| 1521995 | 4/1969 | France. |
| 1283087 | 7/1972 | United Kingdom. |

Primary Examiner—Shep K. Rose
Attorney, Agent, or Firm—Herbert S. Sylvester; Murray M. Grill; Norman Blumenkopf

[57] ABSTRACT

An oral composition effective to promote oral hygiene containing as an anticalculus agent a water soluble oligomer of the formula

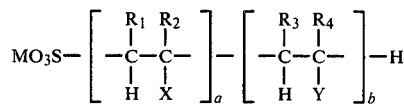

wherein
M is a water soluble orally acceptable cation;
$R_1$, $R_2$, $R_3$ and $R_4$ are independently H, methyl or ethyl;
Y is at least one hydrophilic member of the group consisting of $-COOM_1$, $-CONH_2$, and $-CH_2OH$:
X is at least one hydrophobic member of the group consisting of $-CN$, $-COOR$, $-COOR_5OR$, $-CONHR$, $-COONHR_5COR$, and $-OOCR$;
$M_1$ is H or M;
R is $C_{1-8}$ alkyl;
$R_5$ is $C_{1-4}$ alkylene;
a is 0–7; and
a+b is about 4–15.

10 Claims, No Drawings

ANTICALCULUS ORAL COMPOSITION

This application is a continuation-in-part of our application Ser. No. 755,895 filed Dec. 30, 1976, now U.S. Pat. No. 4,110,429 the entire disclosure of which is incorporated herein by reference.

This invention relates to oral compositions containing an anticalculus agent.

Calculus is a hard, mineralized formation which forms on the teeth. Regular brushing prevents a rapid build-up of these deposits; but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline hydroxyapatite is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including hydroxyapatite. It is apparent therefore that agents which effectively interfere with crystalline growth of hydroxyapatite will be effective as anticalculus agents. A suggested mechanism by which the anticalculus agents of this invention inhibit calculus formation probably involves an increase of the activation energy barrier thus inhibiting the transformation of precursor amorphous calcium phosphate to hydroxyapatite.

Studies have shown that there is a good correlation between the ability of a compound to prevent hydroxyapatite crystalline growth in vitro and its ability to prevent calcification in vivo.

A substantial number of different types of compounds and compositions have been developed for use as antibacterial, and antiplaque and anticalculus agents in oral compositions, including for example such cationic materials as the bis-biquanide compounds and quaternary ammonium compounds, e.g., benzethonium chloride and cetyl pyridinium chloride, disclosed in our parent application Ser. No. 755,895, now U.S. Pat. No. 4,110,429. These cationic materials however tend to stain the teeth with continued use.

It is an object of this invention to provide an improved anticalculus oral composition which will have relatively little or no tendency to stain the teeth.

A further object of the invention is to provide an oral composition which inhibits the transformation of amorphous calcium phosphate to hydroxyapatite crystal structure normally associated with calculus.

Another object of this invention is the provision of an improved method for inhibiting the formation of calculus.

Other objects and advantages will appear as the description proceeds.

In accordance with certain of its aspects, this invention relates to an oral composition comprising an oral (orally acceptable) vehicle containing in an effective amount as an anticalculus agent at least one water soluble oligomer of the formula:

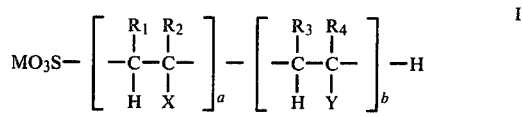

wherein

M is a water soluble orally acceptable cation;

$R_1$, $R_2$, $R_3$ and $R_4$ are independently H, methyl or ethyl;

Y is at least one hydrophilic member of the group consisting of $-COOM_1$, $-CONH_2$, and $-CH_2OH$;

X is at least one hydrophobic member of the group consisting of $-CN$, $-COOR$, $-COOR_5OR$, $-CONHR$, $-COONHR_5COR$, $M_1$ is H or M;

R is $C_{1-8}$ alkyl;

$R_5$ is $C_{1-4}$ alkylene;

a is 0–7; and a+b is about 4–15.

Oligomers of the above formula and methods for their production are disclosed in U.S. Pat. No. 3,646,099 and U.S. Pat. No. 3,859,260, which disclosures are incorporated herein by reference thereto. These oligomers anionic and of relatively low and accurately regulated degree of polymerization, [in contrast to the conventional free radical redox polymerization conducted with an oxidative initiator such as hydrogen, alkyl, or acyl peroxides, persulfates or hydroperoxides in relatively large amounts and a reductive activator such as $NaHSO_3$, $Na_2S_2O_3$, $Na_2S_2O_4$ or sodium formaldehyde sulfoxylate in relatively low amounts generally added subsequently to the polymerization medium] are prepared by a reductive polymerization in which a much larger amount of a bisulfite salt, e.g., $NaHSO_3$ (sodium bisulfite, sodium acid sulfite), a reducing agent, is the initiator charged initially with the monomer, and an oxidizing agent is added in smaller amounts as the activator during the polymerizing or oligomerizing process.

Subscript a in formula I represents the number of moles of hydrophobic groups, and subscript b the number of moles of hydrophilic groups, in the oligomer molecule. The proportion of X (i.e., the value of a) must be small enough, or even zero, to avoid the production of a too large, sticky and hydrophobic polymer molecule, and will of course be dependent for the most part in any particular instance on the identity of the X and Y groups, i.e., the hydrophobic-containing and hydrophilic-containing monomeric reactants. Mixtures of such oligomers may of course also be employed.

Examples of monomers containing hydrophilic Y groups are acrylic acid, methacrylic acid, alpha-ethylacrylic acid, beta-methylacrylic acid, alpha, beta-dimethylacrylic acid, orally acceptable salts ($M_1$) of these acids, for example those containing such cations as alkali metal (e.g., sodium and potassium), ammonium, $C_{1-18}$ mono-, di- and tri-substituted ammonium (e.g., alkanol substituted such as mono-, di- and tri-ethanolammonium), etc., acrylamide, methacrylamide, ethacrylamide, and allyl alcohol and the like.

Examples of monomers containing hydrophobic X groups are acrylonitrile, methacrylonitrile, ethacrylonitrile, methyl and ethyl and octyl acrylate and methacrylate, methoxyethyl acrylate, octoxyethyl methacrylate, ethoxybutyl methacrylate, propoxymethyl acrylate, N-ethylacrylamide, N-isopropylacrylamide, N-methylacrylamide, N-isooctylmethacrylamide, N-propylethacrylamide, vinyl acetate, propionate and octanoate, diacetone acrylamide and the like.

The oligomerization is carried out in water in the presence of a relatively large amount of the bisulfite reducing initiator, expressed in mols of monomer/gram formula weight (gFW) of reducing initiator is about 4 to 15, this ratio determining the degree of oligomerization.

The reductive initiator is preferably a water soluble bisulfite salt, (M in formula I), especially alkali metal such as sodium or potassium, but bisulfite salts containing other orally acceptable cations of the type referred to above may be employed.

In practice, enough oxidative activator is used to effect 100% conversion of the monomers to oligomers. The amount of such activator, expressed as gFW activator/gFW initiator may range from 0.0001 to 0.1 but usually is from about 0.001 to 0.1. Examples of these oxidative activators are ammonium, sodium and potassium persulfate, hydrogen peroxide and other water soluble oxidants commonly employed in the polymerization art.

Following completion of the oligomerization reaction, any free carboxylic acid groups in the oligomer molecules may if desired be partially or completely neutralized, preferably at least 60%, by treating the aqueous oligomer solution with a suitable base to convert such groups to their salts with orally acceptable cations as referred to above. These aqueous oligomer solutions have a highly desirable low viscosity, and low molecular weight range depending on the monomer units in the oligomer.

It will be understood that Formula I above is not intended to depict the actual structure of the oligomer molecule, the bracketed units of which formula are randomly distributed in the molecule with the $-SO_3M$ group being normally bonded to a terminal carbon atom in the oligomer chain devoid of X and or Y substituents. In the oligomers preferred for use herein, a is zero, Y is $-COOM_1$, $R_1-R_4$ are H, and M and $M_1$ are alkali metal, e.g. sodium, b being about 10, as derived from acrylic acid. An oligomer of formula I above in the form of its sodium salt, with a molecular weight of about 1,000, containing about 10 acrylic acid monomeric units, is commercially available under the trade name ND-2 (a product of UniRoyal).

The concentration of these oligomer anticalculus agents in oral compositions can range widely, typically upward from about 0.01% by weight with no upper limit except as dictated by cost or incompatibility with the vehicle. Generally, concentrations of about 0.01% to about 10% and preferably about 0.5% to 2% by weight are utilized. Oral compositions which in the ordinary course of usage could be accidentally ingested preferably contain lower concentrations of these agents. Thus, a mouthwash in accordance with this invention preferably contains less than about 1 weight % of the agent. Dentrifice compositions, topical solutions and prophylactic pastes, the latter to be administered professionally, can preferably contain about 0.1 to 2 weight % of the agent.

The oligomeric anticalculus agents of this invention are antinucleating agents, oral compositions of this invention containing such agents are effective in reducing formation of dental calculus without unduly calcifying the dental enamel, and in contrast to the above-mentioned cationic antibacterial, anti-plaque and anticalculus agents, such agents and compositions have little or no tendency to stain the teeth.

In certain highly preferred forms of the invention the oral composition may be substantially liquid in character, such as a mouthwash or rinse. In such a preparation the vehicle is typically a water-alcohol mixture desirably including a humectant as described below. Generally, the ratio of water to alcohol is in the range of from about 1:1 to about 17:3, by weight. The total amount of water alcohol mixture in this type of preparation is typically in the range of from about 70% to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel. The pH can be controlled with acid (e.g., citric acid or benzoic acid) or base (e.g., sodium hydroxide) or buffered (as with phosphate buffers). Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations generally contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicate, silica, bentonite, and mixtures thereof. Preferred polishing materials include crystalline silica having particle sizes of up to 5 microns, a mean particle size of up to 1.1 microns, and a surface area of up to 50,000 cm²/gm. silica gel, complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 20% to about 99% by weight of the oral preparation. Preferably, it is present in amounts ranging from about 20% to about 75% in toothpaste, and from about 70% to about 99% in toothpowder.

In the preparation of toothpowders, it is usually sufficient to admix mechanically, e.g., by milling, the various solid ingredients in appropriate quantities and particle sizes.

In pasty oral preparations the above-defined oligomer should be compatible with the other components of the preparation. Thus, in a toothpaste, the liquid vehicle may comprise water and humectant typically in an amount ranging from about 10% to about 90% by weight of the preparation. Glycerine, propylene glycol, sorbitol, or polyethylene glycol 400 may also be present as humectants or binders. Particularly advantageous liquid ingredients comprise mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gumlike materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to about 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0, may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

Organic surface-active agents are used in the compositions of the present invention to achieve increased prophylactic action, assist in achieving thorough and complete dispersion of the anti-calculus agents throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid esters of 1.2 dihydroxy propane sulfonate, and the substantially saturated higher aliphatic acyl amides of lower aliphatic amino carboxylic acid compounds, such as those having 12 to 16 carbons in the fatty acid, alkyl, or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g., aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g., sorbitan monosterate) and polypropyleneoxide (i.e., Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005% to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013% to 0.1% and most preferably about 0.0013% to 0.5%, by weight, of fluoride ion.

Various other materials may be incorporated in the oral preparations of this invention such as whitening agents, preservatives, silicones, chlorophyll compounds, other anticalculus agents, antibacterial antiplaque agents, and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, and saccharine. Suitably, flavor and sweetening agents may together comprise from about 0.01% to 5% or more of the preparation.

In preparing the oral compositions of this invention, it is preferred but not essential to add the oligomer after the other ingredients (except perhaps some of the water) are mixed or contacted with each other to avoid a tendency for said agent to be precipitated.

For instance, a mouthrinse or mouthwash may be prepared by mixing ethanol and water with flavoring oil, surfactant, humectant sweetener, color and then the above-defined oligomer, followed by additional water as desired.

A toothpaste may be prepared by forming a gel with humectant, gum or thickener such as hydroxyethyl cellulose, sweetener and adding thereto polishing agent, flavor, additional water, and then the above-defined oligomer. If sodium carboxymethyl cellulose is employed as the gelling agent the procedure of either U.S. Pat. No. 3,842,168 or U.S. Pat. No. 3,843,779, modified by the inclusion of the oligomer, is followed.

In the practice of this invention an oral composition according to this invention such as a mouthwash or toothpaste containing the defined oligomer in an amount effective to inhibit calculus on dental surfaces is applied regularly to dental enamel, preferably from about 5 times per week to about 3 times daily, at a pH of about 4.5 to about 9, generally about 5.5 to about 8, preferably about 6 to 8.

The following specific examples are further illustrative of the nature of the present invention, but it is understood that the invention is not limited thereto. All amounts and proportions referred to herein and in the appended claims are by weight unless otherwise indicated.

EXAMPLE A

The procedure of Example 1 of U.S. Pat. No. 3,646,099 is followed, the initial charge to the reactor being 3.12 g $NaHSO_3$ (0.03 gFW), 159.8 g. water, and 20.74 g. acrylic acid (0.288 mol) as the sole monomer, a correspondingly equivalent amount of the $(NH_4)_2S_2O_8$ activator being employed. The ratio of mols of monomer to gFW $NaHSO_3$ is 9.6, and the oligomer, fully neutralized with 5 N NaOH at the completion of the reaction, may be represented by the formula

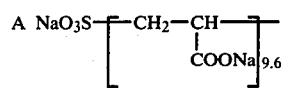

In this case, a in formula I above is zero and b is 9.6 (average). A clear solution is obtained, this Oligomer A having a molecular weight of about 1,000.

EXAMPLE I

Inhibition of Crystal Growth of HAP

This is evaluated by a pH Stat method. 1.0 ml of an aqueous solution of $1 \times 10^{-4}M$ to $1 \times 10^{-5}M$ of the anticalculus agent being tested and 0.1 M sodium dihydrogen phosphate is placed in a reaction flash with 22 to 23 ml. of distilled water with continuous stirring in an atmosphere of nitrogen. To this is added 1 ml. of 0.1 M $CaCl_2$ and the pH adjusted to $7.4 \pm 0.05$ (final conc. of $Ca^{++}$ and $PO_4^{3-} = 4 \times 10^{-3}M$). Consumption of 0.1 N NaOH is recorded automatically by a pH Stat (Radiometer). In this test, the formation of HAP occurs in 2 distinct phases. First rapid base consumption (1–4 min.) then diminishes until 15–20 minutes when second rapid uptake takes place. A delay in the time of second rapid consumption or a total absence of the second rapid consumption indicates an interference with the crystal growth of HAP. Agents which interfere with HAP crystal growth are effective anti-calculus agents. When subjected to the foregoing procedure, Oligomer A above is found to delay the formation of the second phase by more than 12 hours, while Acrysol A-5 polyacrylic acid and sodium polyacrylic acid have no affect.

It is thus clear that Oligomer A effectively inhibits the crystal growth of HAP and that the inhibition is not merely due to the complexation or chelation of calcium from the system since the ratio of inhibitor to total calcium is 1:40 to 1:80.

In the following examples illustrative of mouthwash formulations according to the invention, BC refers to benzethonium chloride, and Pluronic F108 is a polyalkene oxide block polymer.

| | Example | | | |
|---|---|---|---|---|
| | 2 | 3 | 4 | 5 |
| Flavor | 0.22% | 0.22% | 0.22% | 0.22% |
| Ethanol | 15.0 | 15.0 | 15.0 | 15.0 |
| Pluronic F108 | 3.0 | 3.0 | 3.0 | 3.0 |
| Glycerine | 10.0 | 10.0 | 10.0 | 10.0 |
| Na Saccharin | 0.03 | 0.03 | 0.03 | 0.03 |
| Oligomer A | 0.1 | 0.2 | 0.5 | 1.0 |
| Water q.s. to | 100 | 100 | 100 | 100 |
| pH (with NaOH) | 7.4 | 7.4 | 7.4 | 7.4 |
| Appearance | Clear | Clear | Clear | Clear |

The following examples are illustrative of anticalculus toothpastes according to the invention:

| Example | (6) | (7) |
|---|---|---|
| Silica | 30 | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| Oligomer A | 2 | 1 |
| Sodium saccharin | 0.17 | 0.17 |
| Flavor | 0.8 | 0.8 |
| Water q.s. to | 100 | 100 |

Significant reductions in calculus are also obtained according to the present invention when Oligomer A in the above examples is replaced by any of the co-oligomers prepared by the procedures of Examples I–XIII of U.S. Pat. Nos. 3,646,099 and 3,859,260 suitably adjusted to yield a co-oligomer of formula I above in which a is 0–7 and a+b is about 4–15.

EXAMPLE 8

In the study on 16 beagles, a placebo mouthrinse of water at a pH of 7.0 and a 1% aqueous solution of Oligomer A as the test anticalculus mouthrinse are evaluated for effectiveness against formation of calculus for a 6 week period.

16 beagles are given thorough dental prophylaxis in order to remove existing soft and hard deposits. Disclosing solution is used to assure that the teeth are free of such deposits. The animals are assigned to 2 groups of 8 each. The teeth of one group is sprayed with the placebo and the teeth of the other group is sprayed with the test mouthrinse twice a day, 5 days a week, for 6 weeks. At the end of this period, the teeth are scored for calculus on a scale of 1 to 3, as follows:

| Scale | Calculus Formation |
|---|---|
| 1.0 | ⅓ of teeth covered with calculus |
| 2.0 | ⅔ of teeth covered with calculus |
| 3.0 | all of teeth covered with calculus |

The following results are found:

| | Mean Calculus per tooth | % change | Significance* |
|---|---|---|---|
| placebo | 1.50 | — | — |
| Oligomer A mouthrinse | 1.01 | −32.6 | 95% |

*data analyzed by the analysis of variance (Student's t test)

The above results show that a mouthrinse containing Oligomer A according to the invention is significantly effective in reducing calculus formation.

EXAMPLE 9

In this study on 20 rats, a placebo of water at a pH of 7.0 and an 0.1% aqueous solution of Oligomer A as the test anticalculus mouthrinse are evaluated for effectiveness against formation of calculus for a 30 day period.

Litter matured Osborne Mendel rats are used. They are kept on Calculogenic Diet 580F supplemented with 0.2% P as $Na_2HPO_4$. From 21 days onwards, 100 microliters of the placebo and of the test mouthrinse are each applied to the molars of a group of 10 such rats daily for a period of 30 days. The animals are weighed at the beginning and at the end of the study to assure that the rats remain in otherwise normal condition. At the end of the period, calculus formation is assessed according to routine procedures and the following results are found:

| | No. Animals | Weight Gain (gms) | Mean Calculus Units | Significance |
|---|---|---|---|---|
| placebo | 10 | 128 | 17.9 | — |
| Oligomer A mouthrinse | 10 | 131 | 14.9 | at 99% level |

The above results establish that a mouthrinse containing Oligomer A according to the invention is significantly effective in reducing calculus formation.

This invention has been described with respect to preferred embodiments and it will be understood that modifications and variations thereof obvious to those skilled in the art are to be included within the spirit and purview of this application and the scope of the appended claims.

What is claimed is:

1. An oral composition comprising an orally acceptable vehicle containing in an effective amount as an anticalculus agent at least one water soluble oligomer of the formula

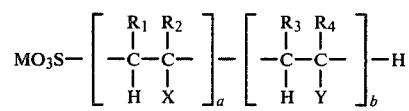

wherein
M is a water soluble orally acceptable cation;
$R_1$, $R_2$, $R_3$ and $R_4$ are independently H, methyl or ethyl;
Y is at least one hydrophilic member of the group consisting of $-COOM_1$, $-CONH_2$, and $-CH_2OH$;
X is at least one hydrophobic member of the group consisting of $-CN$, $-COOR_5OR$, $-CONHR$, $-COONHR_5COR$, and $-OOCR$;
$M_1$ is H or M;
R is $C_{1-8}$ alkyl;
$R_5$ is $C_{1-4}$ alkylene;
a is 0–7; and
a+b is about 4–15.

2. The oral composition of claim 1 wherein said oligomer is present in amount of about 0.01% to about 10% by weight.

3. The oral composition of claim 1 wherein, in said formula, a is zero, 1+b is about 10, Y is $-COOM_1$, $R_1$, $R_2$, $R_3$ and $R_4$ are H, and M and $M_1$ are sodium.

4. The oral composition of claim 1 wherein said vehicle is an aqueous-alcohol and said composition is a mouthwash of pH of about 4.5 to about 9.

5. The oral composition of claim 1 wherein said vehicle comprises a liquid vehicle and a gelling agent and a dentally acceptable polishing material is present and said composition is a toothpaste of pH of about 4.5 to about 9.

6. A method of inhibiting the formation of dental calculus comprising applying to teeth a calculus-inhibiting amount of a composition as defined in claim 1.

7. A method of inhibiting the formation of dental calculus comprising applying to teeth a calculus-inhibiting amount of a composition as defined in claim 2.

8. A method of inhibiting the formation of dental calculus comprising applying to teeth a calculus-inhibiting amount of a composition as defined in claim 3.

9. A method of inhibiting the formation of dental calculus comprising applying to teeth a calculus-inhibiting amount of a composition as defined in claim 4.

10. A method of inhibiting the formation of dental calculus comprising applying to teeth a calculus-inhibiting amount of a composition as defined in claim 5.

* * * * *